United States Patent
Ruan et al.

(10) Patent No.: US 9,683,073 B2
(45) Date of Patent: Jun. 20, 2017

(54) METHOXYPOLYETHYLENE GLYCOL-POLYLACTIC ACID BLOCK COPOLYMER AND PREPARATION METHOD THEREOF

(71) Applicant: SUZHOU HIGH-TECH BIOSCIENSE CO., LTD, Taicang, Suzhou (CN)

(72) Inventors: Junshan Ruan, Suzhou (CN); Pengfei Du, Suzhou (CN); Limian Wang, Suzhou (CN); Huan Zhou, Suzhou (CN)

(73) Assignee: Suzhou High-Tech Bioscience Co., Ltd, Taicang, Suzhou (CN)

( * ) Notice: Subject to any disclaimer, the term of this patent is extended or adjusted under 35 U.S.C. 154(b) by 0 days.

(21) Appl. No.: 14/897,504

(22) PCT Filed: Jul. 16, 2014

(86) PCT No.: PCT/CN2014/082293
§ 371 (c)(1),
(2) Date: Dec. 10, 2015

(87) PCT Pub. No.: WO2015/120693
PCT Pub. Date: Aug. 20, 2015

(65) Prior Publication Data
US 2016/0137775 A1 May 19, 2016

(30) Foreign Application Priority Data

Feb. 14, 2014 (CN) .......................... 2014 1 0050783
Jul. 10, 2014 (CN) .......................... 2014 1 0326099

(51) Int. Cl.
| | | |
|---|---|---|
| A61K 9/16 | (2006.01) |
| C08G 63/08 | (2006.01) |
| A61K 9/10 | (2006.01) |
| A61K 9/51 | (2006.01) |
| A61K 47/34 | (2017.01) |
| A61K 9/19 | (2006.01) |
| A61K 31/337 | (2006.01) |
| A61K 9/107 | (2006.01) |
| C08G 63/81 | (2006.01) |
| C08G 63/85 | (2006.01) |
| C08G 63/664 | (2006.01) |
| C08L 67/04 | (2006.01) |

(52) U.S. Cl.
CPC .............. *C08G 63/08* (2013.01); *A61K 9/10* (2013.01); *A61K 9/1075* (2013.01); *A61K 9/19* (2013.01); *A61K 9/5153* (2013.01); *A61K 31/337* (2013.01); *A61K 47/34* (2013.01); *C08G 63/664* (2013.01); *C08G 63/81* (2013.01); *C08G 63/85* (2013.01); *C08L 67/04* (2013.01)

(58) Field of Classification Search
CPC ......... C08L 67/04; A61K 9/5153; A61K 9/10; C08G 63/08
See application file for complete search history.

(56) References Cited

U.S. PATENT DOCUMENTS

| | | | |
|---|---|---|---|
| 6,616,941 B1 * | 9/2003 | Seo ...................... | A61K 9/1075 424/427 |
| 2012/0121711 A1 * | 5/2012 | Hu ....................... | A61K 9/5153 424/489 |

FOREIGN PATENT DOCUMENTS

| | | | |
|---|---|---|---|
| CN | 1644215 | * | 7/2005 |
| CN | 102219892 | | 10/2011 |
| CN | 102274163 | * | 12/2011 |
| CN | 102885772 | | 1/2013 |

OTHER PUBLICATIONS

Wan et al "Biodegradable poly(l-lactide)-poly(ethylene glycol) multiblock copolymer:synthesis and evaluation of cell affinity", Biomaterials 24 (2003) 2195-2203, Jul. 2003.*
Dong et al (In vitro and in vivo evaluation of methoxy polyethylene glycol-polylactide (MPEG-PLA) nanoparticles for small-molecule drug chemotherapy, Biomaterials 28 (2007) 4154-4160), Available online Jun. 18, 2007.*
Znan et al (Cyclic RGD conjugated poly(ethylene glycol)-co-poly(lactic acid) micelle enhances paclitaxel anti-glioblastoma effect, Journal of Controlled Release 143 (2010) 136-142), Available online Jan. 7, 2010.*
International Search Report filed in PCT/CN2014/082293 mailed Nov. 27, 2014.

* cited by examiner

*Primary Examiner* — Gregory Listvoyb
(74) *Attorney, Agent, or Firm* — Rankin, Hill & Clark LLP

(57) ABSTRACT

A methoxypolyethylene glycol-polylactic acid block copolymer is disclosed, the methoxypolyethylene glycol-polylactic acid block copolymer being a block copolymer formed by ring opening polymerization of D,L-lactide and methoxypolyethylene glycol. A mass ratio of the methoxypolyethylene glycol to the D,L-lactide is 1:0.55-0.65 or 1:0.73-0.89 or 1:0.91-0.99. A preparation method of the foregoing block copolymer is also provided. When the block copolymer is used as a carrier for preparing a drug micelle, the encapsulation efficiency of the drug micelle prepared after being re-dissolved by water can be greater than 90% at 12 hours.

7 Claims, 6 Drawing Sheets

METHOXYPOLYETHYLENE GLYCOL-POLYLACTIC ACID BLOCK COPOLYMER AND PREPARATION METHOD THEREOF

TECHNICAL FIELD

The present invention belongs to the field of polymer material synthesis, and more particularly, relates to a methoxypolyethylene glycol-polylactic acid block copolymer and a preparation method thereof.

BACKGROUND

Drug delivering methods based on nanometer technologies in recent years have gained great attentions of researchers. Wherein, a nanometer micelle carrier system formed by self-assembly of amphiphilic block copolymer in an aqueous solution has become a new-type drug carrier having great application prospect. A methoxypolyethylene glycol-polylactic acid block copolymer is a biodegradable material, which can be widely applied to various dosage forms, and is finally degraded into carbon dioxide and water in a human body, and a methoxypolyethylene glycol-dl-polylactic acid block copolymer with a certain molecular weight can form a micelle. These micelles after being prepared into dosage forms with bulk drugs have the advantages of slow release, target, safety, easy absorption and small side effects.

A nano-polymer micelle is a drug carrier system developed in recent years directing to indissolvable drugs, which has a core-shell structure, wherein the core is a hydrophobic part, and the shell is a hydrophilic part. The polymer micelle may encapsulate the indissolvable drugs into the core part to solubilize the indissolvable drugs. Compared with a normal solubilizer and latent solvent, the polymer micelle drug carrier system has higher security since it selects biodegradable material as raw materials. Therefore, it has a better application prospect while being served as an encapsulating-carrying accessory for the indissolvable drugs.

There are two synthesis methods at present for preparing polyether and polyester block copolymers: one method is to add polyether into a pre-dried polymerization bottle and residual moisture in the polyether is removed by means of heating and evacuation, then lactone is added, and catalyst is added when the polyether and lactone are in a molten state, and the polymerization bottle is sealed for reaction. The method has the defects that a reaction system is unavoidably contacted with the outside during the process of adding the lactone and catalyst, which is extremely easy to bring the moisture in the air into the reaction system, while the lactone is easily hydrolyzed in the molten state. Another method is to use polyether to be directly polycondensed with lactic acid under high temperature to obtain a block copolymer, but it has defects that the polymerization activity of the lactic acid is lower, and a large number of lactic acid is remained in the final product, wherein the residual lactic acid monomer needs to be removed through multiple and repeated dissolution-precipitation; therefore, not only the final copolymer yield is lower, but also the stability between each batch of products is poorer, and harmful heavy metal catalyst cannot be effectively removed during the repeated precipitation process. Moreover, the product is easily oxidized and turns yellow because the polycondensation temperature is higher and the reaction time is longer. Patent 2011100637853 discloses a method for preparing medical polyether polyester block copolymer, which includes using sufficiently dried polyether to initiate ring opening polymerization of lactone under a vacuum condition to prepare a block copolymer, wherein a degree of vacuum is required to be less than 1 mm Hg, a polymerization process is controlled to be performed at a temperature more than 130° C., and a polymerization time is 1-12 hours (h); after the reaction is finished, un-reacted monomer remained in the product is removed through hydration, and the heavy metal catalyst is removed through a method of high speed centrifugation, so that a copolymer material with good molecular weight homogeneity is prepared. This copolymer while being used for carrying drugs effectively improves the solubility of indissolvable drugs, and improves the safety and efficacy of the drugs. However, it has defects that the stability after being dispersed by water is poorer, and drugs are leaked in a very short time, so that it cannot be further popularized and truly applied during clinic application since its physical stability is not high. In order to solve the problem, CN201010114289 discloses a technology which improves the stability of a micelle after re-dissolving through a method of adding amino acid in a polymer micelle, but the added substances have higher requirements on industrialized production, and a stabilizer added increases the technical complexity of the preparation, and meanwhile, the added amino acid plays a role of degrading the main drugs, which is not suitable for large-scale production.

SUMMARY

Object of the invention: in order to solve the technical problems existed in the prior art, the present invention provides a methoxypolyethylene glycol-polylactic acid block copolymer, wherein a micelle formed by the copolymer after being re-dissolved by water has good stability, and the encapsulation efficiency of the micelle after being dispersed by water can be greater than 90% at 12 h.

Another technical problem to be solved by the present invention is to provide a preparation method of the foregoing methoxypolyethylene glycol-polylactic acid block copolymer and applications thereof.

Technical content: to fulfill the foregoing technical object, the present invention adopts the following technical solution.

A methoxypolyethylene glycol-polylactic acid block copolymer is a block copolymer formed by ring opening polymerization of D,L-lactide and methoxypolyethylene glycol, wherein a mass ratio of the methoxypolyethylene glycol to the D,L-lactide is 1:0.55-0.65 or 1:0.73-0.89 or 1:0.91-0.99. The mass ratio of the methoxypolyethylene glycol to the D,L-lactide has a great influence on the encapsulation efficiency of the micelle formed by the synthesized block copolymer and re-dissolved by water, therefore, the dosage of the methoxypolyethylene glycol and the D,L-lactide needs to be controlled strictly.

A preparation method of the foregoing methoxypolyethylene glycol-polylactic acid block copolymer includes the following steps of:

weighing D,L-lactide and methoxypolyethylene glycol with a formula ratio for standby application, subjecting methoxypolyethylene glycol with a formula ratio to vacuum drying for 2-8 h at 60-130° C. in a reactor, performing nitrogen displacement, then adding the D,L-lactide with a formula ratio, then adding a metal catalyst, then performing evacuation, performing nitrogen displacement for three times after the D,L-lactide is completely melted, then performing evacuation, ensuring that the reactor has a negative pressure and is sealed or protected by nitrogen, then raising temperature to 125-150° C., reacting for 6-20 h, thus obtaining a pale yellow clear viscous liquid after the reaction is completed; adding an organic solvent in the pale yellow clear viscous liquid for dissolution, stirring for 30-50 minutes (min), then continuously adding ice-cold anhydrous diethyl ether and stirring for 20-40 min, standing for 12-24 h at 0-5° C., then performing suction filtration and finally performing vacuum drying, thus obtaining the methoxypolyethylene glycol-polylactic acid block copolymer.

Wherein, the molecular weight of the methoxypolyethylene glycol is 1000-20000. Preferably, the molecular weight of the methoxypolyethylene glycol is 2000 or 5000.

The catalyst is stannous octoate, wherein the mass of the stannous octoate occupies 0.05 wt %-0.5 wt % of the total mass of the D,L-lactide and the methoxypolyethylene glycol.

Preferably, the organic solvent is any one or more of acetonitrile, methanol, acetone, methylene chloride, dimethylformamide, dimethyl sulfoxide, tetrahydrofuran, acetone, short chain fatty alcohol and ethyl acetate, and the dosage of the organic solvent is that 0.2-1 ml of the organic solvent is added per 1 g of the pale yellow clear viscous liquid.

Wherein preferably, the dosage of the anhydrous ice diethyl ether is that 5-10 ml of anhydrous ice diethyl ether is added per 1 g of the pale yellow clear viscous liquid.

Advantageous effects: according to the present invention, the block copolymer prepared by methoxypolyethylene glycol and D,L-lactide with a proper mass ratio is employed as a carrier material and applied to prepare a drug polymer micelle lyophilized preparation, wherein the encapsulation efficiency of the lyophilized preparation prepared after being re-dissolved by water can be greater than 90% at 12 h, the effect of which is far better than that of a common lyophilized preparation, and complies with the actual situations of clinic drug application, thus satisfying clinic requirements.

DETAILED DESCRIPTION

The foregoing contents of the invention will be further explained in details by means of experimental examples hereinafter, but it should not be understood that the scope of the foregoing subject of the invention is only limited to the following examples, and any technology implemented based on the foregoing contents of the invention shall all fall within the scope of the invention.

Embodiment 1: preparation of methoxypolyethylene glycol-polylactic acid block copolymer.

(1) 51.07 g of D,L-lactide and 50.57 g of methoxypolyethylene glycol 2000 were weighed for standby application, the methoxypolyethylene glycol 2000 was subjected to vacuum drying for 7 h under 100 □, nitrogen displacement was performed, D,L-lactide was added, and 0.2 g of catalyst stannous octoate was added, evacuation was performed to a vacuum degree of 0.096 Mpa, a reaction temperature was maintained at 100° C., nitrogen displacement was performed for three times after the D,L-lactide was completely fused, evacuation was performed, the reactor was ensured to have a negative pressure and was sealed, then the temperature was raised to 140° C., and reaction was performed for 12 h, thus obtaining a pale yellow clear viscous liquid after the reaction was completed.

Figure 1:
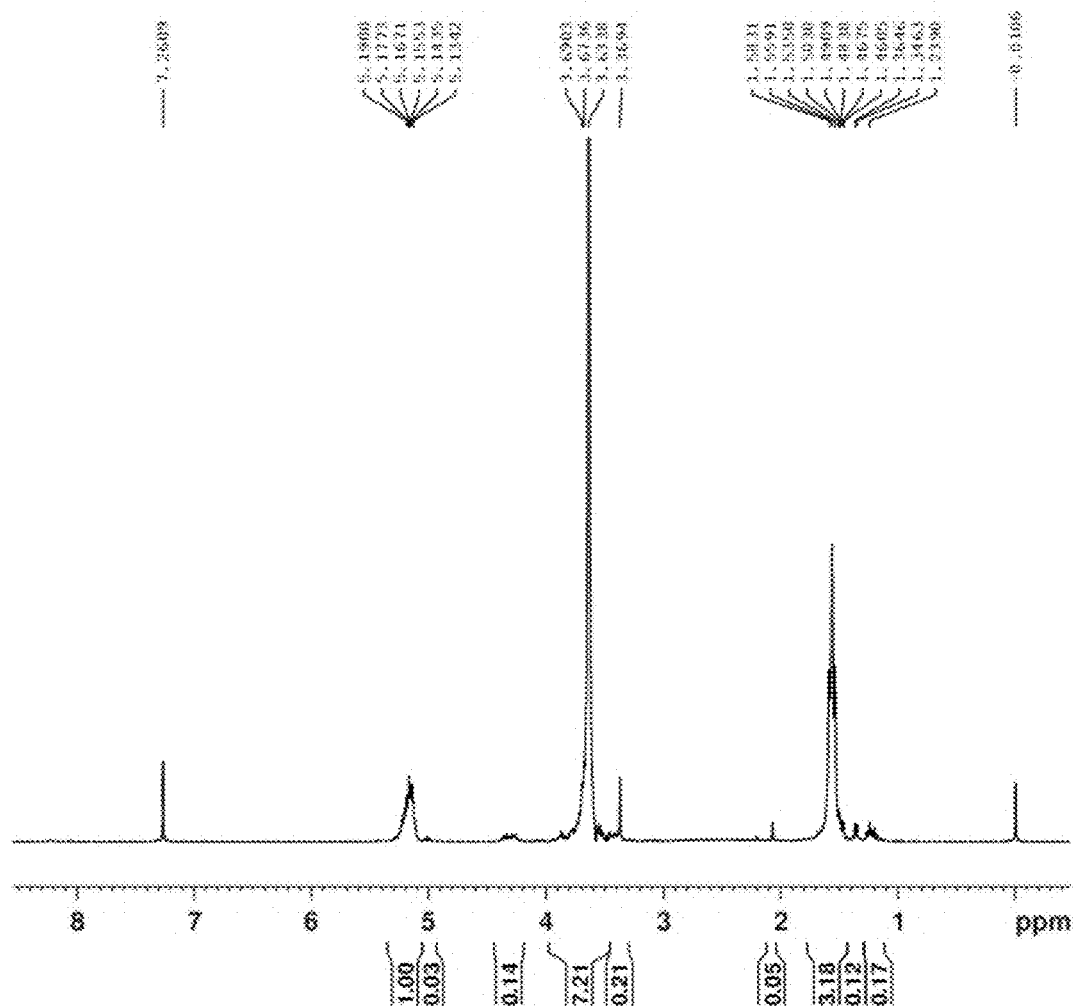
FIG. 1 is a CDCl$_3$ $^1$HNMR spectrum of a methoxypolyethylene glycol polylactic acid block copolymer.
Figure 2:
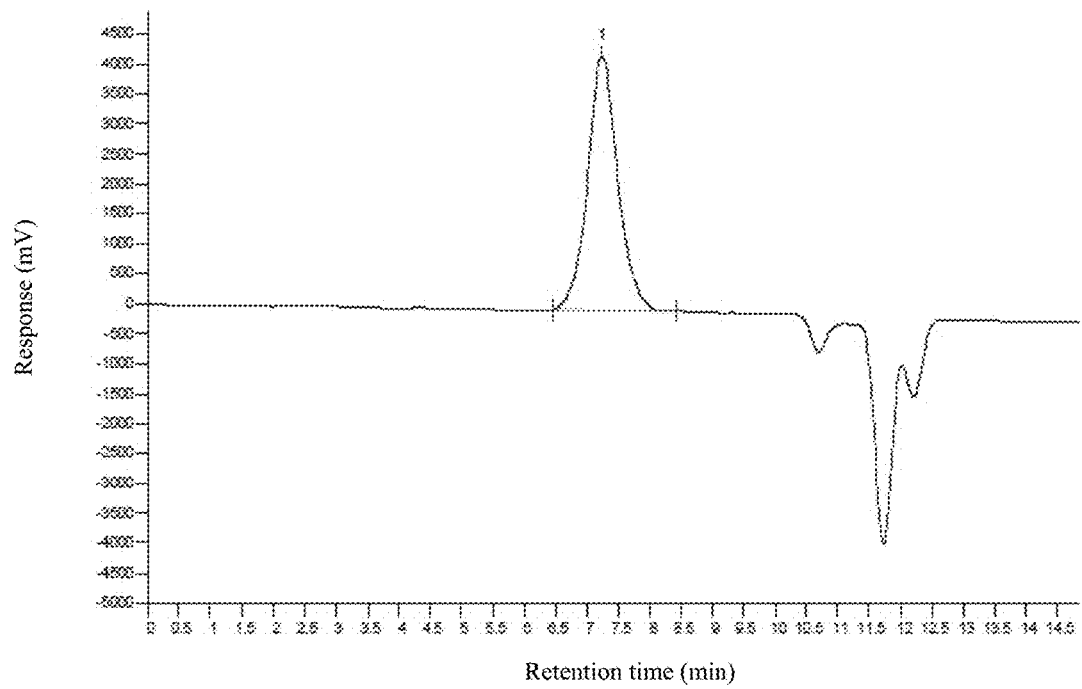
FIG. 2 is a GPC profile of the methoxypolyethylene glycol polylactic acid block copolymer.

(2) 25 ml of methylene chloride was added into the pale yellow clear viscous liquid obtained in step (1), and stirred for 30 min; then 510 ml of anhydrous ice diethyl ether was added, and stirred for 30 min; then standing was performed for 12 h under 0° C., vacuum drying was performed after suction filtration, thus obtaining the methoxypolyethylene glycol-polylactic acid block copolymer; refining was performed for three times according to the foregoing operation process to obtain the methoxypolyethylene glycol-polylactic acid block copolymer, wherein the total yield was about 75%. The obtained polymer was characterized using nuclear magnetic resonance and gel chromatography, wherein the results were as shown in FIG. 1 and FIG. 2. FIG. 1 is the characterization of various hydrogens in the methoxypolyethylene glycol-polylactic acid block copolymer, proving that the methoxypolyethylene glycol-polylactic acid block copolymer is synthesized. The detection results of FIG. 2 are as follows: Mp: 6330; Mn: 5887; Mw: 6374; Mz: 6873; $M_{z+i}$: 7393; Mv: 6301; and PDI: 1.08272.

Embodiment 2: preparation of methoxypolyethylene glycol-polylactic acid block copolymer.

(1) 48.77 g of D,L-lactide and 51.27 g of methoxypolyethylene glycol 2000 were weighed for standby application, the methoxypolyethylene glycol 2000 was subjected to vacuum drying for 5 h under 120° C., nitrogen displacement was performed, D,L-lactide was added, and then 0.048 g of catalyst stannous octoate was added, evacuation was performed to a vacuum degree of 0.095 Mpa, a reaction temperature was maintained at 120° C., nitrogen displacement was performed for three times after the D,L-lactide was completely fused, evacuation was performed, the reactor was ensured to have a negative pressure and protected by nitrogen, then the temperature was raised to 140° C., and reaction was performed for 14 h, thus obtaining a pale yellow clear liquid after the reaction was completed.

(2) 29 ml of methylene chloride was added into the foregoing pale yellow clear liquid for dissolution, and was stirred and dissolved; then 586 ml of anhydrous ice ethyl ether was added, and stirred for 30 min; standing was performed for 12 h under 5° C., then vacuum drying was performed after suction filtration. Refining was performed for three times according to the foregoing operation process to obtain the methoxypolyethylene glycol-polylactic acid block copolymer, wherein the total yield was about 85%.

Embodiment 3: preparation of methoxypolyethylene glycol-polylactic acid block copolymer.

(1) 47.53 g of D,L-lactide and 52.17 g of methoxypolyethylene glycol 2000 were weighed for standby application, the methoxypolyethylene glycol 2000 was subjected to vacuum drying for 7h under 130° C., nitrogen displacement was performed, 0.3 g of catalyst stannous octoate was added and then D,L-lactide was added, evacuation was performed to a vacuum degree of 0.093 Mpa, a reaction temperature was maintained at 130° C., nitrogen displacement was performed for three times after the D,L-lactide was completely fused, evacuation was performed, the reactor was ensured to have a negative pressure and was sealed, then the temperature was raised to 150° C., and reaction was performed for 6 h, thus obtaining a pale yellow clear liquid after the reaction was completed.

(2) 45 ml of methylene chloride was added into the foregoing pale yellow clear liquid in step (1), and was stirred and dissolved; then 550 ml of anhydrous ice ethyl ether was added, and stirred for 30 min; standing was performed for 12 h under 0° C., then vacuum drying was performed after suction filtration. Refining was performed for three times according to the foregoing operation process to obtain the methoxypolyethylene glycol-polylactic acid block copolymer, wherein the total yield was about 80%.

Embodiment 4: preparation of methoxypolyethylene glycol-polylactic acid block copolymer.

(1) 47.11 g of D,L-lactide and 52.85 g of methoxypolyethylene glycol 2000 were weighed for standby application, the methoxypolyethylene glycol 2000 was subjected to vacuum drying for 4 h under 120° C., D,L-lactide was added, and then 0.4 g of catalyst stannous octoate was added, evacuation was performed to a vacuum degree of 0.093 Mpa, a reaction temperature was maintained at 120° C., after the D,L-lactide was completely fused, evacuation was performed, the reactor was ensured to have a negative pressure and was sealed, then the temperature was raised to 130° C., and reaction was performed for 18h, thus obtaining a pale yellow clear viscous liquid after the reaction was completed.

(2) 40 ml of methylene chloride was added into the foregoing pale yellow clear viscous liquid obtained in step (1) for dissolution, and was stirred for 30 min; then 500 ml of anhydrous ice diethyl ether was added, and stirred for 30 min; standing was performed for 12 h under 0° C., vacuum drying was performed after suction filtration, and refining was performed for three times according to the foregoing operation process to obtain the methoxypolyethylene glycol-polylactic acid block copolymer, wherein the total yield was about 80%.

Embodiment 5: preparation of methoxypolyethylene glycol-polylactic acid block copolymer.

(1) 45.91 g of D,L-lactide and 54.06 g of methoxypolyethylene glycol 2000 were weighed for standby application, the methoxypolyethylene glycol 2000 was subjected to vacuum drying for 3 h under 120° C., nitrogen displacement was performed, then D,L-lactide was added, and 0.25 g of catalyst stannous octoate was added, evacuation was performed, a reaction temperature was maintained at 120° C., after the D,L-lactide was completely fused, nitrogen displacement was performed for three times, the reactor was ensured to have a negative pressure and was sealed, then the temperature was raised to 140° C., and reaction was performed for 12 h, thus obtaining a pale yellow clear viscous liquid after the reaction was completed.

(2) 50 ml of methylene chloride was added into the pale yellow clear viscous liquid obtained in step (1), and stirred for 30 min; then 500 ml of anhydrous ice diethyl ether was added, and stirred for 30 min; standing was performed for 12 h under 0° C., vacuum drying was performed after suction filtration, and refining was performed for three times according to the foregoing operation process to obtain the methoxypolyethylene glycol-polylactic acid block copolymer, wherein the total yield was about 75%.

Embodiment 6: preparation of methoxypolyethylene glycol-polylactic acid block copolymer.

(1) 44.45 g of D,L-lactide and 55.68 g of methoxypolyethylene glycol 2000 were weighed for standby application, the methoxypolyethylene glycol 2000 was subjected to vacuum drying for 5 h under 110° C., nitrogen displacement was performed, then D,L-lactide was added, and 0.36 g of catalyst stannous octoate was added, evacuation was performed to a vacuum degree of 0.09 Mpa, a reaction temperature was maintained at 110° C., after the D,L-lactide was completely fused, evacuation was performed, the reactor was ensured to have a negative pressure and was sealed, the temperature was controlled to be raised to 140° C., and reaction was performed for 14 h, thus obtaining a pale yellow clear viscous liquid after the reaction was completed.

(2) 60 ml of methylene chloride was added into the pale yellow clear viscous liquid obtained in step (1), and stirred for 30 min; then 660 ml of anhydrous ice diethyl ether was added, and stirred for 30 min; standing was performed for 12 h under 0° C., vacuum drying was performed after suction filtration, and refining was performed for three times according to the foregoing operation process to obtain the methoxypolyethylene glycol-polylactic acid block copolymer, wherein the total yield was about 80%.

Embodiment 7: preparation of methoxypolyethylene glycol-polylactic acid block copolymer.

(1) 39.51 g of D,L-lactide and 61.77 g of methoxypolyethylene glycol 2000 were weighed for standby application, the methoxypolyethylene glycol 2000 was subjected to vacuum drying for 6h under 100° C., nitrogen displacement was performed, then D,L-lactide was added, and 0.08 g of catalyst stannous octoate was added, evacuation was performed to a vacuum degree of 0.098 Mpa, a reaction temperature was maintained at 100° C., after the D,L-lactide was completely fused, evacuation was performed, the reactor was ensured to have a negative pressure and was sealed, the temperature was controlled to be raised to 140° C., and reaction was performed for 12 h, thus obtaining a pale yellow clear viscous liquid after the reaction was completed.

(2) 50 ml of methylene chloride was added into the pale yellow clear viscous liquid obtained in step (1), and stirred for 30 min; then 540 ml of anhydrous ice diethyl ether was added, and stirred for 30 min; standing was performed for 12 h under 0° C., vacuum drying was performed after suction filtration, and refining was performed for three times according to the foregoing operation process to obtain the methoxypolyethylene glycol-polylactic acid block copolymer, wherein the total yield was about 70%.

Embodiment 8: preparation of methoxypolyethylene glycol-polylactic acid block copolymer.

(1) 42.17 g of D,L-lactide and 57.89 g of methoxypolyethylene glycol 2000 were weighed for standby application, the methoxypolyethylene glycol 2000 was subjected to vacuum drying for 8 h under 100° C., nitrogen displacement was performed, D,L-lactide was added, and then 0.45 g of catalyst stannous octoate was added, evacuation was performed to a vacuum degree of 0.095 Mpa, a reaction temperature was maintained at 100° C., after the D,L-lactide was completely fused, evacuation was performed, the reactor was ensured to have a negative pressure and was sealed, the temperature was controlled to be raised to 130° C., and reaction was performed for 10 h, thus obtaining a pale yellow clear viscous liquid after the reaction was completed.

(2) 75 ml of methylene chloride was added into the pale yellow clear viscous liquid obtained in step (1) for dissolution, and stirred for 30 min; then 720 ml of anhydrous ice diethyl ether was added, and stirred for 30 min; standing was performed for 12 h under 0° C., vacuum drying was performed after suction filtration, and refining was performed for three times according to the foregoing operation process to obtain the methoxypolyethylene glycol-polylactic acid block copolymer, wherein the total yield was about 80%.

Embodiment 9: preparation of methoxypolyethylene glycol-polylactic acid block copolymer.

(1) 37.53 g of D,L-lactide and 62.71 g of methoxypolyethylene glycol 2000 were weighed for standby application, the methoxypolyethylene glycol 2000 was subjected to vacuum drying for 6 h under 110° C., nitrogen displacement was performed, then D,L-lactide was added, and 0.1 g of catalyst stannous octoate was added, evacuation was performed to a vacuum degree of 0.085 Mpa, a reaction temperature was maintained at 110° C., after the D,L-lactide was completely fused, evacuation was performed, the reactor was ensured to have a negative pressure and was sealed, the temperature was controlled to be raised to 140° C., and reaction was performed for 6 h, thus obtaining a pale yellow clear viscous liquid after the reaction was completed.

(2) 40 ml of methylene chloride was added into the pale yellow clear viscous liquid obtained in step (1), and stirred for 30 min; then 556 ml of anhydrous ice diethyl ether was added, and stirred for 30 min; standing was performed for 12 h under 0° C., vacuum drying was performed after suction filtration, and refining was performed for three times according to the foregoing operation process to obtain the methoxypolyethylene glycol-polylactic acid block copolymer, wherein the total yield was about 80%.

Embodiment 10: preparation of methoxypolyethylene glycol-polylactic acid block copolymer.

(1) 35.54 g of D,L-lactide and 64.68 g of methoxypolyethylene glycol 2000 were weighed for standby application, the methoxypolyethylene glycol 2000 was subjected to vacuum drying for 7 h under 100° C., nitrogen displacement was performed, D,L-lactide was added, and then 0.08 g of catalyst stannous octoate was added, evacuation was performed to a vacuum degree of 0.098 Mpa, nitrogen displacement was performed, and a reaction temperature was maintained at 100° C., after the D,L-lactide was completely fused, evacuation was performed, and nitrogen protection is performed, the temperature was controlled to be raised to 140° C., and reaction was performed for 12 h, thus obtaining a pale yellow clear viscous liquid after the reaction was completed.

(2) 35 ml of methylene chloride was added into the pale yellow clear viscous liquid obtained in step (1) for dissolution, and stirred for 30 min; then anhydrous ice diethyl ether was added according to a ratio of 5 to 1 between the volume of the anhydrous ice diethyl ether and the weight of the pale yellow clear viscous liquid (i.e., ml/g) for extraction, and stirred for 30 min; standing was performed for 12 h under 0° C., vacuum drying was performed after suction filtration, and refining was performed for three times according to the foregoing operation process to obtain the methoxypolyethylene glycol-polylactic acid block copolymer, wherein the total yield was about 85%.

Embodiment 11: preparation of docetaxel nano-polymer micelle lyophilized preparation.

The block polymer prepared by the present invention is used as a carrier to prepare a drug nano-polymer micelle, wherein the steps are as follows:

(1) 20 g of docetaxel, 400g (mPEG2000: PLA=1:0.99) of methoxypolyethylene glycol-polylactic acid block copolymer prepared in embodiment 1, 4000 ml of water, and 400 ml of organic solvent acetonitrile were taken for standby application. (2) 1000 ml of acetonitrile was added into standby docetaxel for ultrasound dissolution; then 400 g of methoxypolyethylene glycol-polylactic acid block copolymer was added for continuous dissolution, and then aseptic filtration was performed; then rotary evaporation was performed for 2h under 50° C. and a rotation velocity of 80 r/min to boil off acetonitrile and obtain a docetaxel polymer gel film, 4000 g of 50° C. water was added quickly for vortex hydration, the temperature of the micelle solution was quickly reduced to 5° C. after complete hydration to obtain the micelle solution, then the micelle solution was subjected to aseptic filtration, sub-packaged and lyophilized.

Embodiments 12: characterization of docetaxel nano-polymer micelle lyophilized preparation.

Figure 3:
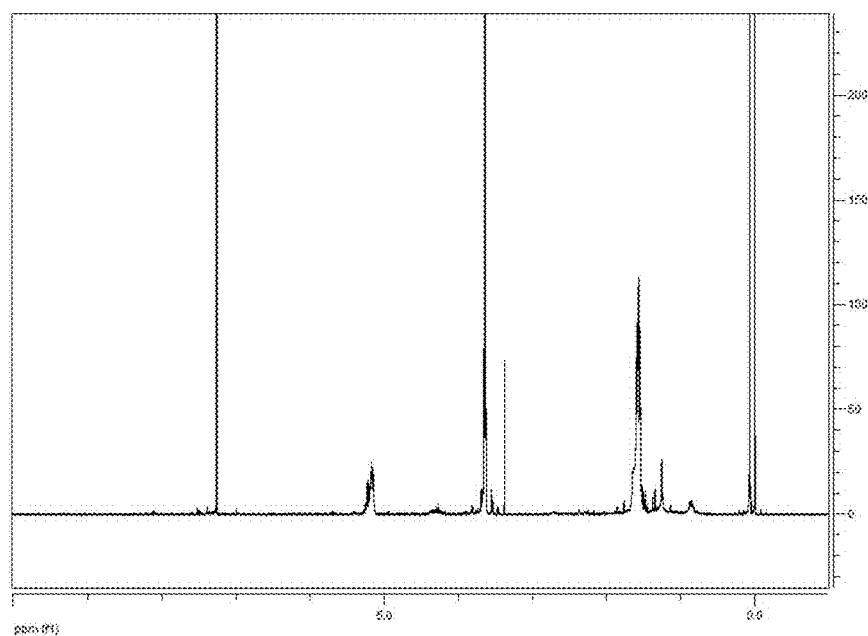
FIG. 3 is a CDCl$_3$ $^1$HNMR spectrum of a docetaxel polymer micelle lyophilized preparation.
Figure 4:
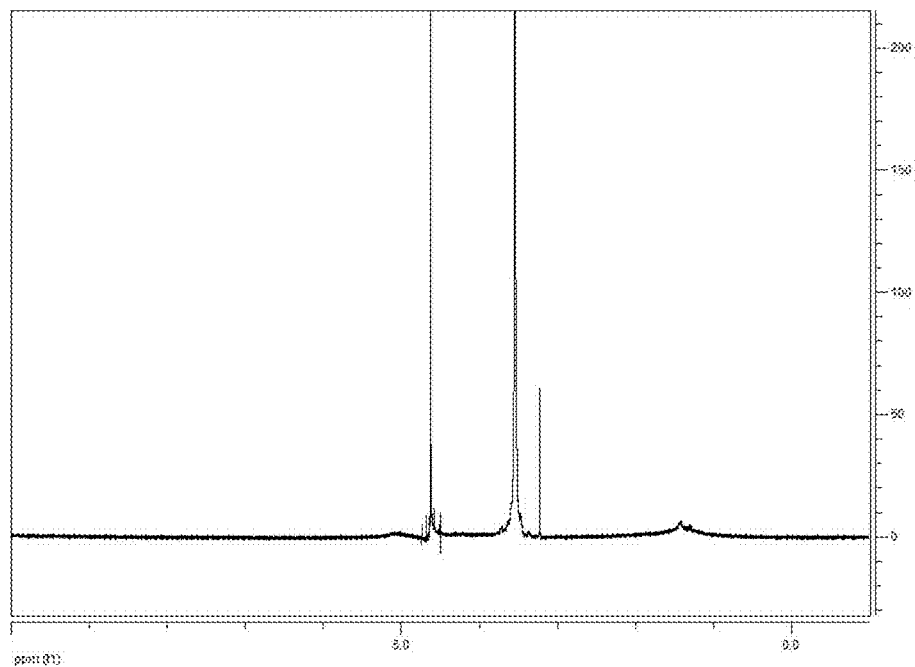
FIG. 4 is a D2O 1HNMR spectrum of the docetaxel polymer micelle lyophilized preparation.
Figure 5:
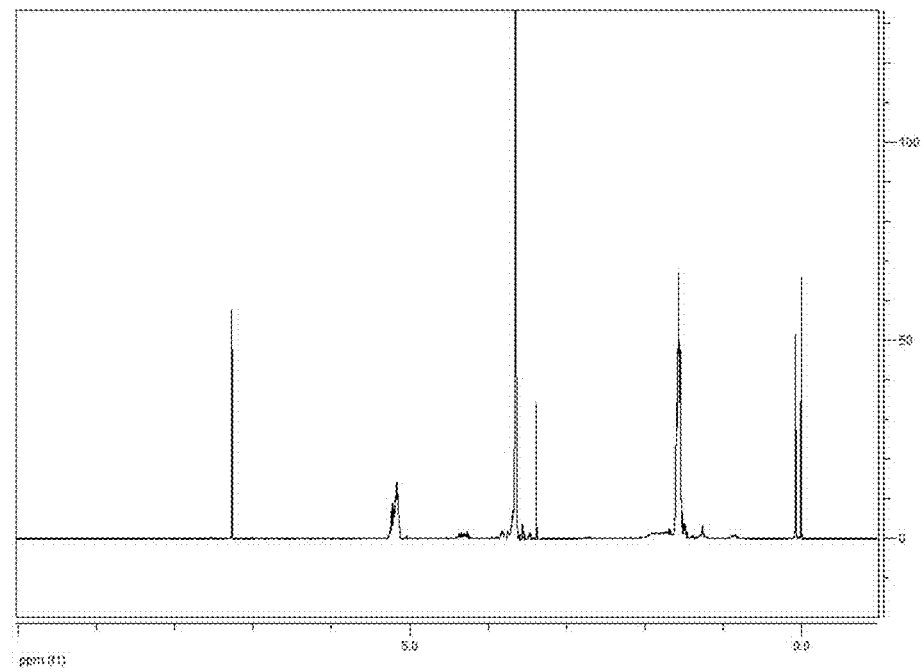
FIG. 5 is a CDCl$_3$ $^1$HNMR spectrum of the methoxypolyethylene glycol polylactic acid block copolymer.

(1) FIG. 3 is a $CDCl_3$ $^1HNMR$ spectrum of the docetaxel nano-polymer micelle lyophilized preparation prepared in embodiment 11, FIG. 4 is a $D_2O$ $^1HNMR$ spectrum of the docetaxel polymer micelle lyophilized preparation prepared in embodiment 11, and FIG. 5 is a $CDCl_3$ $^1HNM$ spectrum of the methoxypolyethylene glycol polylactic acid block copolymer prepared in embodiment 1. Results show that the docetaxel was encapsulated in the core of the micelle, and a characteristic absorption peak of the docetaxel in the 1HNMR spectrum of the micelle was not found.

Figure 6:
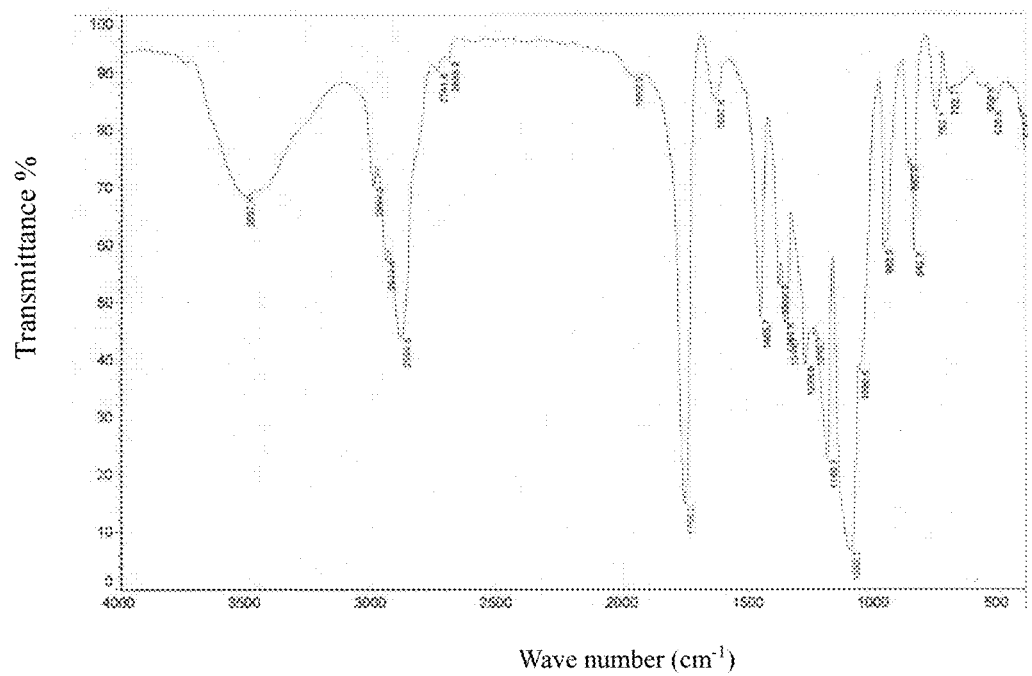
FIG. 6 is an infrared spectrum of the methoxypolyethylene glycol polylactic acid block copolymer.
Figure 7:
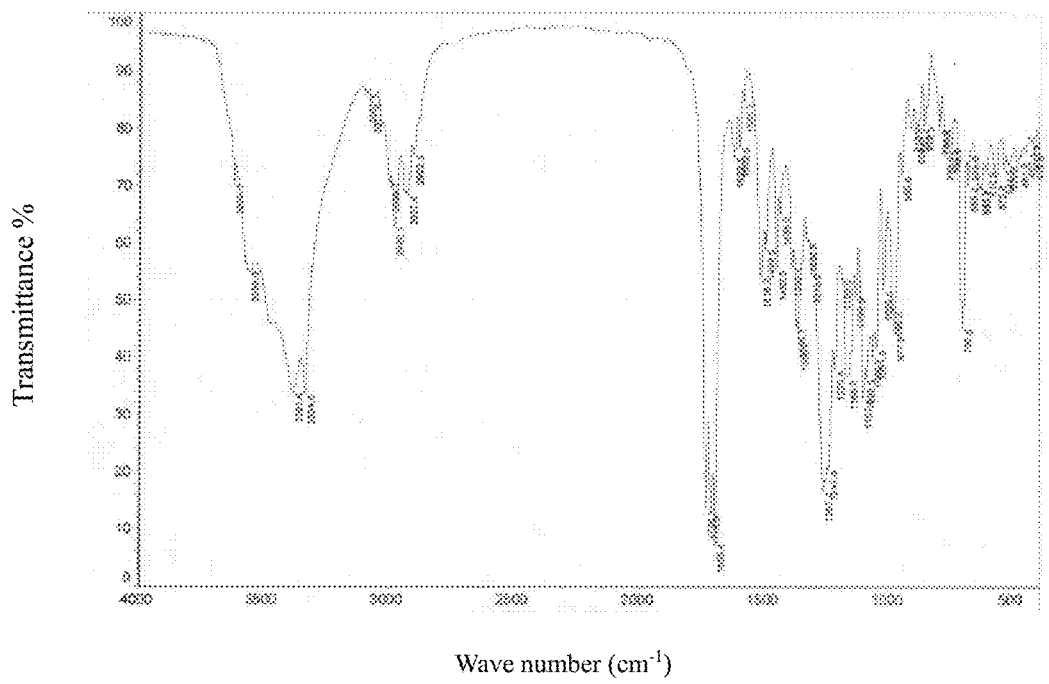
FIG. 7 is an infrared spectrum of docetaxel.
Figure 8:
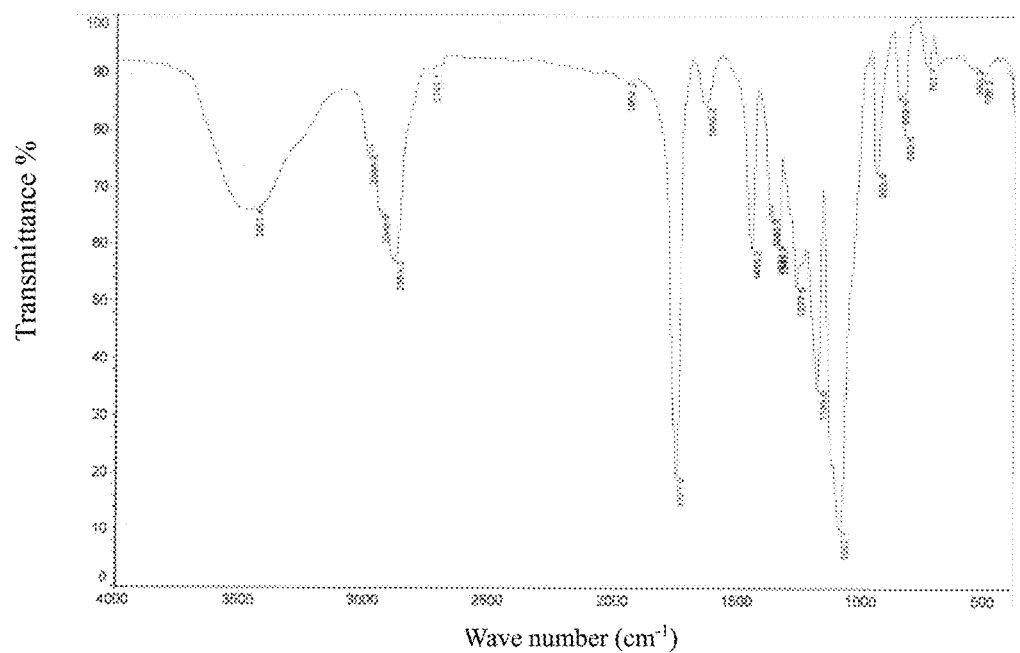
FIG. 8 is an infrared spectrum of a docetaxel polymer micelle.

(2) A small quantity of the docetaxel nano-polymer micelle lyophilized preparation prepared in embodiment 11, docetaxel and the methoxypolyethylene glycol polylactic acid prepared in embodiment 1 were taken to perform Fourier transform infrared spectrum scanning, wherein results as shown in FIG. 6, FIG. 7 and FIG. 8 proved that the docetaxel was encapsulated in the core of the micelle, and a characteristic absorption peak of the docetaxel in the profile of the micelle was not found.

Figure 9:
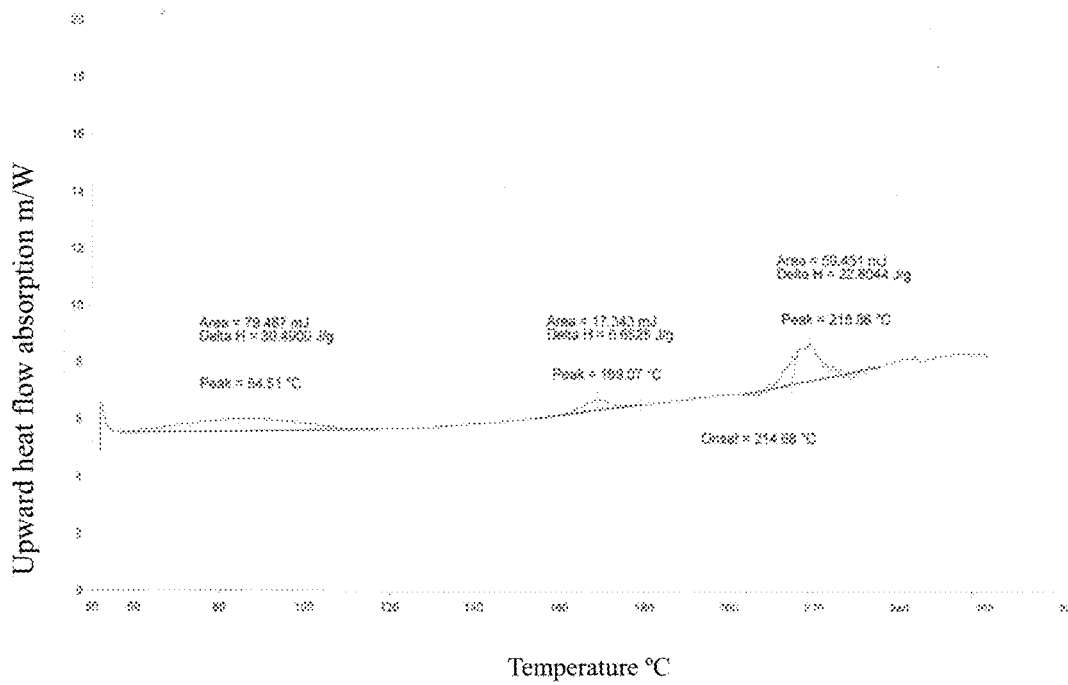
FIG. 9 is a thermal-scanning profile of docetaxel.
Figure 10:
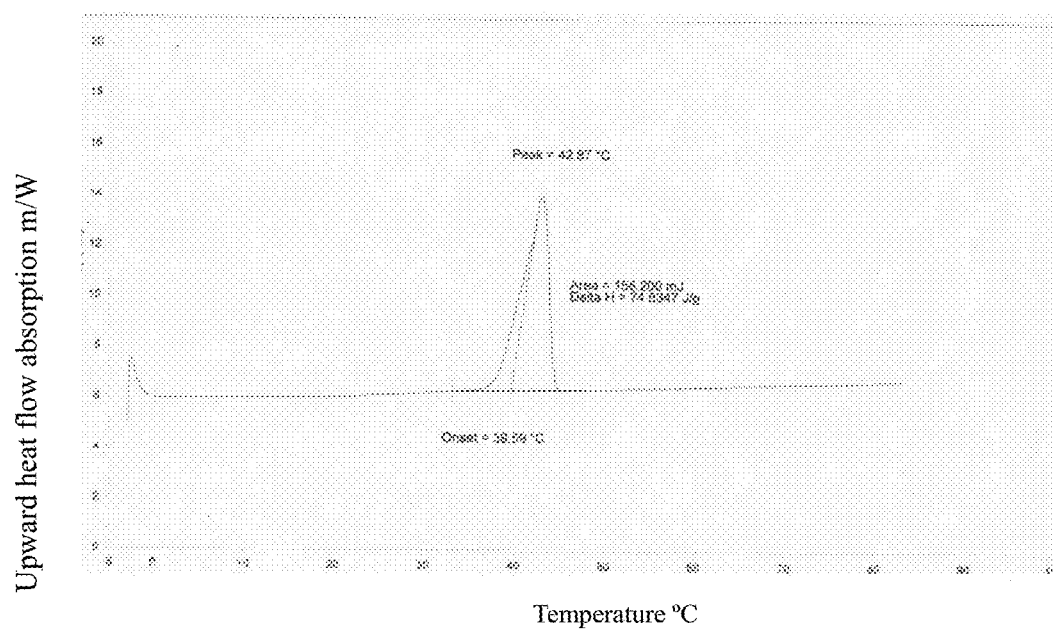
FIG. 10 is a thermal-scanning profile of the methoxypolyethylene glycol polylactic acid block copolymer.
Figure 11:
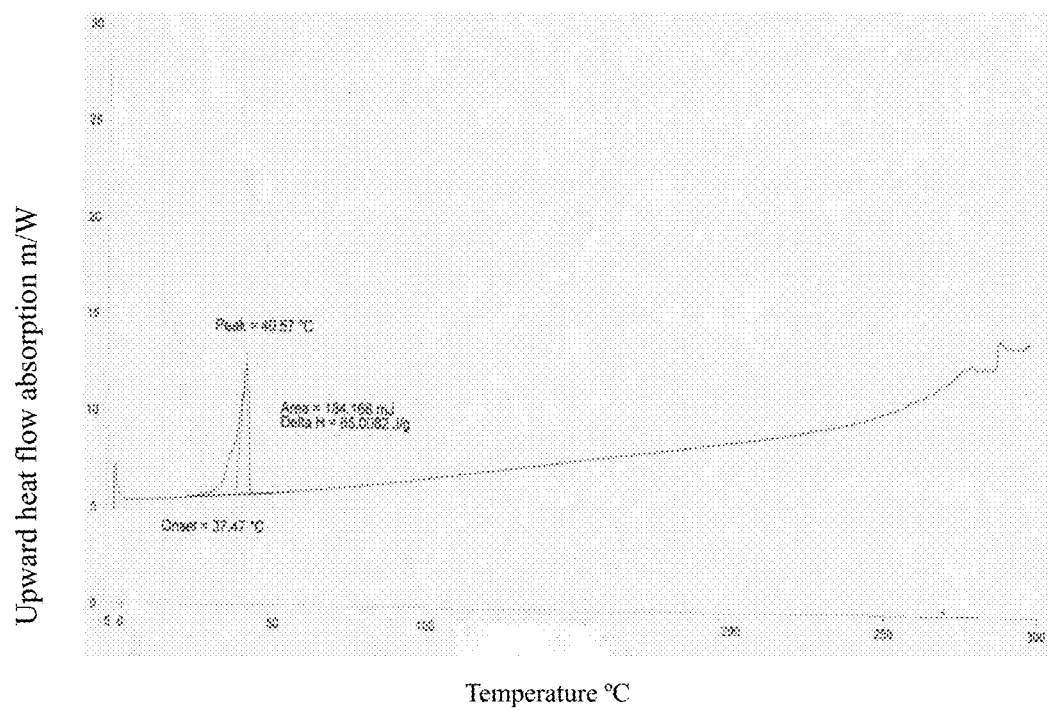
FIG. 11 is a thermal-scanning profile of the docetaxel polymer micelle.

(3) A small quantity of the docetaxel nano-polymer micelle lyophilized preparation prepared in embodiment 11, docetaxel and the methoxypolyethylene glycol polylactic acid prepared in embodiment 1 were taken to perform thermal analysis scanning, wherein results as shown in FIG. 9, FIG. 10 and FIG. 11 proved that the docetaxel was encapsulated in the core of the micelle, and a characteristic absorption peak of the docetaxel in the thermal-scanning profile of the micelle was not found.

Embodiment 13: encapsulation efficiency detection results of docetaxel nano-polymer micelle lyophilized preparation in different time after re-dissolving.

A control drug was prepared according to a recipe 17 (a ratio of polyethylene glycol to polylactic acid is 1:1.2, and a drug-carrying capacity is 6%) in embodiment 1 disclosed in CN201110105540.2. The docetaxel nano-polymer micelle lyophilized preparation was prepared according to the embodiment 11 of the present invention, which was an experimental group, wherein three parallel experiments were performed for the experimental group, and were marked as embodiment 11-1, embodiment 11-2 and embodiment 11-3. Physiological saline was added into the preparation of the control group and the experimental group respectively for dissolution until the concentration was 1 mg/ml (by docetaxel), and then placed under a room temperature (25±2° C.) to detect the encapsulation efficiency thereof in different time. Results were as shown in Table 2.

The encapsulation efficiency of the micelle was measured using high speed centrifugation (10000 r/min, 10 min), wherein the encapsulation efficiency=(1-free drug/total drug) *100%. When determining the encapsulation efficiency of the docetaxel polymer micelle using HPLC, chromatogram conditions used were as follows: ODS was used as a filling material, 0.043mol/L ammonium acetate aqueous solution-acetonitrile (45:55) was used as a mobile phase, and a detection wavelength was 230 nm. Theoretical plate number calculated by a docetaxel peak should not be less than 2000.

TABLE 2

Encapsulation efficiency detection results of docetaxel nano-polymer micelle lyophilized preparation in different time after re-dissolving

| | Time (Hour) | | | | | | | |
|---|---|---|---|---|---|---|---|---|
| | 0 | 0.5 | 1 | 2 | 5 | 8 | 12 | 24 |
| Control group | 96.7% | 55% | 45.2% | 33.7% | 27.6% | 15.1% | 10.2% | 2.5% |
| Embodiment 11-1 | 98.3% | 98% | 98% | 97.4% | 97.3% | 97.1% | 96.9% | 90.3% |
| Embodiment 11-2 | 97.3% | 97.0% | 96.4% | 96.0% | 95.6% | 94.1% | 93.1% | 90.4% |
| Embodiment 11-3 | 98.1% | 97.5% | 95.6% | 95.1% | 94.4% | 93.8% | 92.8% | 90.1% |

As shown in Table 2, the encapsulation efficiency of the drug in the experimental group was still greater than 90% at 24 h, while burst release occurred to the drug in the control group at 0.5 h.

The invention claimed is:

1. A methoxypolyethylene glycol-polylactic acid block copolymer, wherein the methoxypolyethylene glycol-polylactic acid block copolymer is a block copolymer formed by ring opening polymerization of D,L-lactide and methoxypolyethylene glycol, and wherein a mass ratio of the methoxypolyethylene glycol to the D,L-lactide is 1:0.99, and
   wherein when the block copolymer is formed into drug-containing micelles and dispersed in water, the micelles have an encapsulation efficiency of greater than 90% at 24 hours.

2. A method of preparing a methoxypolyethylene glycol-polylactic acid block copolymer, the method comprising:
   weighing D,L-lactide and methoxypolyethylene glycol with a formula ratio for standby application, subjecting methoxypolyethylene glycol with a formula ratio to vacuum drying for 2-8 hours at 60-130° C. in a reactor, performing nitrogen displacement, then adding the D,L-lactide with the formula ratio, then adding a metal catalyst, then performing evacuation, performing nitrogen displacement for three times after the D,L-lactide is completely melted, then performing evacuation, ensuring that the reactor has a negative pressure and is sealed or protected by nitrogen, then raising the temperature to 125-150° C., reacting for 6-20 hours, thus obtaining a pale yellow clear viscous liquid after the reaction is completed; adding an organic solvent in the pale yellow clear viscous liquid for dissolution, stirring for 30-50 minutes, then continuously adding ice-cold anhydrous diethyl ether and stirring for 20-40 minutes, standing for 12-24 hours at 0-5° C., then performing suction filtration and finally performing vacuum drying, thus obtaining the methoxypolyethylene glycol-polylactic acid block copolymer,
   wherein a mass ratio of the methoxypolyethylene glycol to the D,L-lactide is 1:0.99, and
   wherein when the block copolymer is formed into drug-containing micelles and dispersed in water, the micelles have an encapsulation efficiency of greater than 90% at 24 hour.

3. The method according to claim 2, wherein the molecular weight of the methoxypolyethylene glycol is 1000-20000.

4. The method according to claim 2, wherein the catalyst is stannous octoate, and the mass of the stannous octoate is 0.05 wt %-0.5 wt % of the total mass of the D,L-lactide and the methoxypolyethylene glycol.

5. The method according to claim 2, wherein the organic solvent is any one or more of acetonitrile, methanol, acetone, methylene chloride, dimethylformamide, dimethyl sulfoxide, tetrahydrofuran, acetone, short chain fatty alcohol and ethyl acetate, and wherein 0.2-1 ml of the organic solvent is added per 1 g of the pale yellow clear viscous liquid.

6. The method according to claim 2, wherein 5-10 ml of the ice-cold anhydrous diethyl ether is added per 1 g of the pale yellow clear viscous liquid.

7. A methoxypolyethylene glycol-polylactic acid block copolymer,
   wherein the methoxypolyethylene glycol-polylactic acid block copolymer is a block copolymer formed by ring opening polymerization of D,L-lactide and methoxypolyethylene glycol, and wherein a mass ratio of the methoxypolyethylene glycol to the D,L-lactide is 1:0.55-0.65 or 1:0.73-0.89 or 1:0.91-0.99,
   wherein when the block copolymer is formed into drug-containing micelles and dispersed in water, the micelles have an encapsulation efficiency of greater than 90% at 24 hours.

* * * * *